United States Patent [19]
Atkinson et al.

[11] Patent Number: 5,991,032
[45] Date of Patent: Nov. 23, 1999

[54] CONTAMINANT IDENTIFICATION AND CONCENTRATION DETERMINATION BY MONITORING THE INTENSITY OF THE OUTPUT OF AN INTRACAVITY LASER

[75] Inventors: George H. Atkinson; Jeffrey S. Pilgrim, both of Tucson, Ariz.

[73] Assignee: Innovative Lasers Corporation, Tucson, Ariz.

[21] Appl. No.: 09/165,884

[22] Filed: Oct. 2, 1998

[51] Int. Cl.$^6$ ..................................................... G01N 21/31
[52] U.S. Cl. .................... 356/347; 250/339.13; 250/343
[58] Field of Search ................................... 356/300, 326, 356/328, 436, 437; 250/339.12, 339.13, 339.1, 343

[56] References Cited

U.S. PATENT DOCUMENTS

| | | | |
|---|---|---|---|
| 5,650,856 | 7/1997 | Morse | 356/437 |
| 5,689,334 | 11/1997 | Atkinson et al. | 356/326 |
| 5,723,864 | 3/1998 | Atkinson et al. | 250/339.13 |
| 5,747,807 | 5/1998 | Atkinson et al. | 250/339.13 |

OTHER PUBLICATIONS

D.A. Gilmore et al, "Intracavity laser spectroscopy in the 1.38–1.55 $\mu$m spectral region using a multimode $Cr^{4+}$:YAG laser", *Optics Communications*, vol. 103, pp. 370–374 (1993).

D.A. Gilmore et al, "Intracavity absorption spectroscopy with a titanium: sapphire laser", *Optics Communications*, vol. 77, No. 5 & 6, pp. 385–389, Jul. 15, 1990.

G.H. Atkinson et al, "Intracavity laser spectroscopy", *Proc. SPIE Int. Soc. Opt. Eng.*, No. 1637, pp. 126–133 (1992).

*Primary Examiner*—F. L. Evans
*Attorney, Agent, or Firm*—Benman & Collins

[57] ABSTRACT

A method and apparatus for detecting the presence of a specific concentration of gaseous species within a calibrated range in a gas sample are disclosed. The ILS gas detection system of the present invention simply comprises an ILS laser and an optical detector. However, the potential or operational wavelength bandwidth of the ILS laser is preferably entirely included within one of the absorption bands or regions assigned to the intracavity gaseous species being monitored. Thus, within the calibrated range, the presence of the gaseous species changes the output laser intensity of the ILS laser. Consequently, only the intensity of the output of the ILS laser need be monitored in order to quantitatively determine the concentration of the absorbing gaseous species when using the ILS method of the present invention.

24 Claims, 5 Drawing Sheets

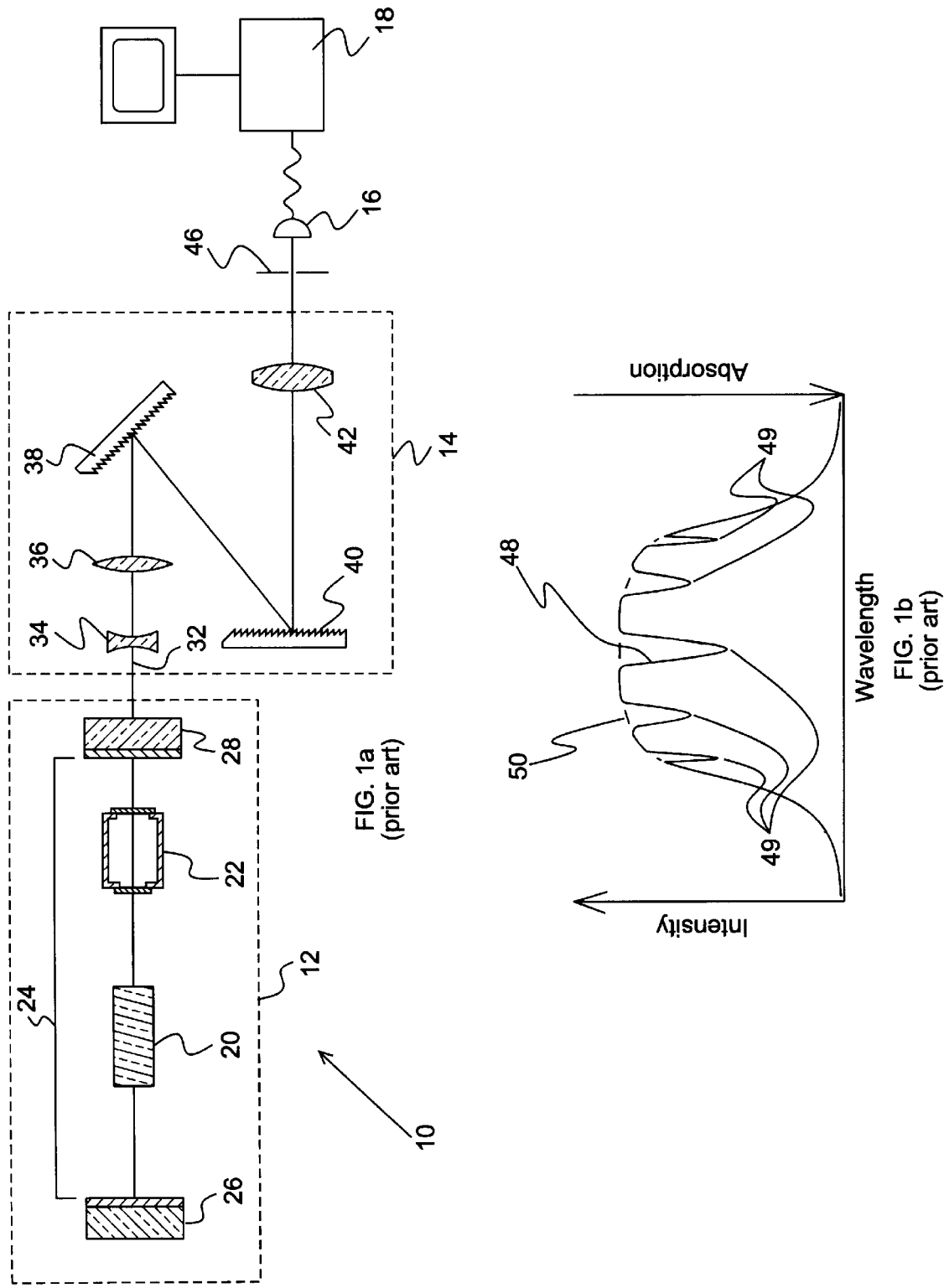

CONTAMINANT IDENTIFICATION AND CONCENTRATION DETERMINATION BY MONITORING THE INTENSITY OF THE OUTPUT OF AN INTRACAVITY LASER

CROSS-REFERENCE TO RELATED APPLICATION

This application is related to application Ser. No. 09/166,003, filed on even date herewith. That application concerns a method for detecting the presence of a specific concentration of gaseous species in a gas sample using an ILS laser with a wavelength-selective element for measuring changes in the spectral output of the sensor. The present application is directed to the use of an ILS laser without any wavelength-selective element(s) whereby the total laser output intensity is used to determine gaseous species concentrations.

TECHNICAL FIELD

This invention relates, generally, to the detection of contaminants in gases, and more particularly, to the high sensitivity detection of gaseous molecules, atoms, radicals, and/or ions by laser techniques generally termed intracavity laser spectroscopy.

BACKGROUND OF THE INVENTION

A laser in its simplest form can be schematically illustrated as including a gain medium that is located between two mirrors. Light within the laser cavity is reflected back and forth between the mirrors, each time passing through the gain medium, which produces optical gain. The mirror coating on the first mirror may be totally reflective, while the mirror coating on the second mirror may be partially reflective, thereby permitting some light to escape from the laser cavity. The spatial region between the reflective surfaces of the mirrors defines the laser resonator or cavity, and in the context of the present invention relates to the so-called "intracavity region".

The intensity of the laser output is a function of both the wavelength region over which the gain medium operates and the reflectivity of the resonator elements. Normally this output is broad and without sharp, distinctive spectral features.

The identification of gaseous species, e.g., atoms, molecules, radicals, or ions, via laser spectroscopy requires that the laser output be in a wavelength region where the species absorbs. In conventional applications of lasers to the detection of gaseous species, laser radiation is used to excite a gas sample that is external to the laser in order to produce a secondary signal such as ionization or fluorescence. Alternatively, in conventional absorption spectroscopy, laser light is passed through a gas sample that is situated outside of the laser and attenuation that varies with wavelength is monitored.

Some twenty years ago, another detection methodology, intracavity laser spectroscopy (ILS) was first explored; see, e.g., G. Atkinson et al, "Detection of Free Radicals by an Intracavity Dye Laser Technique", *Journal Of Chemical Physics*, Vol. 59, pp. 350–354, (Jul. 1, 1973). In ILS, a laser itself is used as the detector. The gas sample to be analyzed is inserted into the optical cavity of a multimode, homogeneously broadened laser. Atkinson et al, supra, showed that by placing gaseous molecules, atoms, radicals, and/or ions in either their ground or excited states inside the optical cavity, the laser output can be altered. In particular, the absorption spectrum of the intracavity species appears in the spectral output of the laser.

Distinct absorption features in the laser output arise from the intracavity losses introduced by the gaseous species that are absorbing. (As used herein, an absorption feature corresponds to a series of consecutive wavelengths where the light intensity reaches a single local minimum in light intensity in a plot of light intensity versus wavelength.) In a multimode laser, intracavity absorption losses compete with the laser gain via the normal mode dynamics. As a result, attenuation can be observed in the laser output intensity at wavelengths where the stronger intracavity absorption features compete effectively against the gain of the laser. The more intense the absorption features, the larger the decrease in the laser output intensity at those wavelengths.

By inserting the absorbing gaseous species inside the laser resonator, ILS can provide a detection sensitivity that is enhanced over conventional spectroscopy methods. The enhanced detection sensitivity of ILS techniques derives from the non-linear competition between (1) the gain produced in the laser gain medium and (2) the absorber loss(es). As a result, ILS can be utilized to detect both weak absorption and/or extremely small absorber concentrations.

Each gaseous species in the optical cavity can be uniquely identified by its respective absorption spectrum or signature. Additionally, the intensity of a specific absorption feature or features in the spectral signature can be used to determine the concentration of the gaseous species once the sensor is appropriately calibrated. (As used herein, the term "spectral signature" corresponds to the wavelength plotted against absorption intensity or absorbance that uniquely identifies the gaseous species.)

The spectral signature of the gaseous species can be obtained by dispersing the output of the ILS laser with respect to wavelength. Two detection schemes are typically employed to disperse the output of the ILS laser and thereby obtain the spectral signature of the gaseous species. The output of the ILS laser can be passed through a fixed-wavelength, dispersive spectrometer, and the specific spectral region that is resolved by this spectrometer can be recorded using a multichannel detector; see U.S. Pat. No. 5,747,807, issued May 5, 1998, to G. H. Atkinson et al entitled "Diode Laser-Pumped Laser System for Ultra-sensitive Gas Detection via Intracavity Laser Spectroscopy (ILS)". Alternatively, a spectrometer that can be scanned in wavelength can be employed to selectively resolve different spectral regions that are recorded with a single channel detector, supra.

Prior art ILS detection systems employ ILS lasers having a spectral bandwidth that is substantially broad relative to the bandwidth of the absorption features in the absorption spectrum of the intracavity species to be detected; see U.S. Pat. No. 5,689,334, issued Nov. 18, 1997, to G. H. Atkinson et al entitled "Intracavity Laser Spectroscope for High Sensitivity Detection of Contaminants". In particular, the laser systems possess an operational wavelength bandwidth that is at least three times as broad as the absorption features of the gaseous species being monitored.

Prior art methods of performing ILS, however, while successfully demonstrated in the laboratory, are too large and complex for many commercial applications. In particular, the requirement for a spectrometer to disperse the spectral output of the laser, as well as for a computer to analyze the absorption features, adds to the size and complexity of the detection system. In contrast, the constraints of commercial reality dictate that a gas detector be conveniently sized, relatively inexpensive, and reliable.

Thus, what is needed is a methodology that significantly reduces (1) the complexity of ILS measurements and (2) the size of ILS instrumentation, for example, by eliminating the need for a spectrometer and a computer.

SUMMARY OF THE INVENTION

In accordance with the present invention, a method for detecting the presence of a specific concentration of a gaseous species in a gas sample is disclosed. The method comprises:

(a) determining that the gaseous species absorbs light within at least one single band of consecutive wavelengths and determining the concentration of the gaseous species within a calibrated range;

(b) providing an ILS laser comprising:
  (i) a laser cavity; and
  (ii) a gain medium,
    wherein the ILS laser is configured to operate only at wavelengths entirely included within the band of consecutive wavelengths where the gaseous species is absorbing, and the absorption induced by the gaseous species is large enough to change the total output intensity of the laser within a calibrated range;

(c) situating the gain medium such that an output beam from the gain medium is directed through the gas sample that is contained in the laser cavity prior to exiting the laser cavity; and (d) situating a detector so as to detect the output exiting the ILS laser to quantify either the absolute output power or the relative change in the laser output power.

Additionally, a gas detection system for detecting the presence of a specific concentration within the calibrated range of a gaseous species in a gas sample, is provided wherein the gaseous species absorbs light within at least one single band of consecutive wavelengths and thereby changes the output intensity exiting the ILS laser by a specific amount. The gas detection system comprises:

(a) an ILS laser comprising:
  (i) a laser cavity; and
  (ii) a gain medium,
    the ILS laser being configured to operate-only at wavelengths entirely included within the band of consecutive wavelengths where the gaseous species is absorbing and the absorption induced by the gaseous species is large enough to change the total output intensity of the laser within a calibrated range;

(b) a container for containing the gas sample in the laser cavity, the container allowing an output beam emanating from the gain medium to pass through the gas sample prior to exiting the laser cavity; and (c) a detector for determining the output intensity exiting the ILS laser to thereby quantify either the absolute output power or the relative change in the laser output power.

In accordance with the present invention, the present inventors have devised a commercially-viable contaminant sensor system that is smaller, simpler, and less expensive to construct than any ILS laser system disclosed in prior art.

Other objects, features, and advantages of the present invention will become apparent upon consideration of the following detailed description and accompanying drawings, in which like reference designations represent like features throughout the figures.

BRIEF DESCRIPTION OF THE DRAWINGS

The drawings referred to in this description should be understood as not being drawn to scale except if specifically noted.

FIG. 1a is a cross-sectional view depicting a prior art gas detection system comprising an ILS laser, a spectrometer assembly, an optical detector, and a computer for analyzing electrical output from the optical detector;

FIG. 1b, on coordinates of intensity and wavelength, is a plot of the spectrally resolved output of the prior art ILS laser both (i) when absorbing gaseous species are present in the laser cavity and (ii) when the absorbing gaseous species are not present within the laser cavity;

DESCRIPTION OF PREFERRED EMBODIMENTS

Figure 2A:
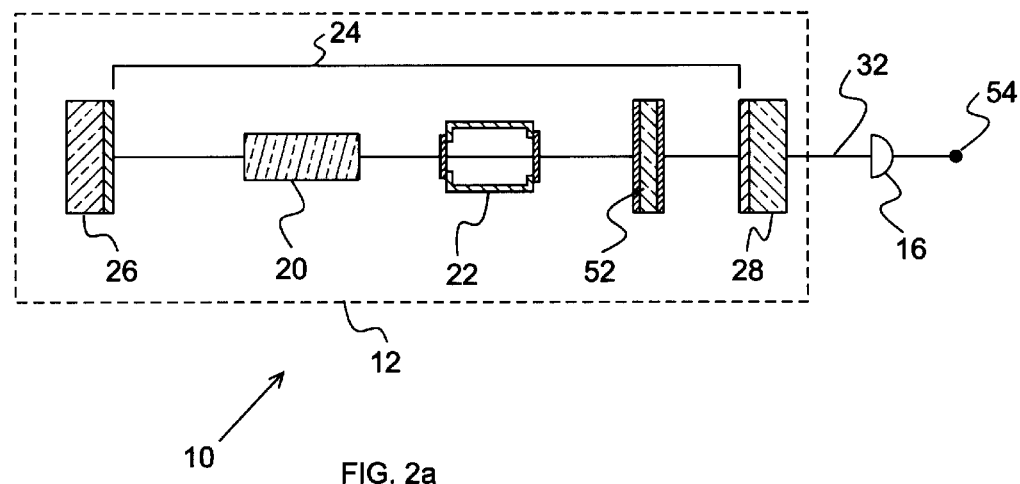
FIG. 2a is a cross-sectional view depicting a gas detection system of the present invention comprising an ILS laser and an optical detector.

Reference is now made in detail to a specific embodiment of the present invention, which illustrates the best mode presently contemplated by the inventors for practicing the invention. Alternative embodiments are also briefly described as applicable.

The present invention is directed to extremely high sensitivity detection of gaseous species using an ILS sensor. The term "gaseous species" as used herein refers to molecular, atomic, radical, and/or ionic species that may be present in gaseous materials such as those that are used in the fabrication of silicon films. Accordingly, the ILS gas detection system of the present invention may be used to detect the presence of a contaminant (e.g., water) in a gaseous material (e.g., nitrogen). Alternatively, ILS detection may be used to determine if a gas line (e.g., nitrogen gas line) has been sufficiently purged of the gaseous material (i.e., nitrogen).

FIGS. 1a and 1b schematically illustrate the prior art method of performing ILS detection. Specifically, in FIG. 1a, a cross-section of an ILS gas detection system 10 is shown comprising an ILS laser 12, a spectrometer assembly 14, an optical detector 16, and a computer 18 for analyzing electrical output from the optical detector.

The ILS laser 12 depicted in FIG. 1a includes a gain medium 20 and a gas sample cell 22 that are situated within an optical resonator 24 defined by the entire optical path length between mirrors 26 and 28. It will be appreciated that the ILS laser 12 additionally requires a pumping source (not shown), such as an optical pumping source that delivers optical radiation to the gain medium 20 to thereby drive the ILS laser 12.

FIG. 1a shows that laser light generated within the gain medium 20 is directed to the gas sample cell 22 and passes through the gas sample therein. As described above, gaseous species within the optical resonator or laser cavity 24 and, in particular, within the gas sample cell 22, may introduce absorption losses if absorption features are located in the wavelength region where the ILS laser 12 operates. Accordingly, the output beam 32 of the ILS laser 12 can be analyzed to identify the presence of an absorbing gaseous species within the laser cavity 24 by determining if the output beam exiting the ILS laser contains absorption features identical to those in the spectral signature of the gaseous species. It will be noted that the spectral signature contains information on intensity and wavelength.

As used herein, an absorption feature corresponds to an absorption line, i.e., a region of consecutive wavelengths observable in a plot of light intensity versus wavelength that includes and surrounds a single local minimum in light intensity (i.e., where absorption reaches a maximum). Each absorption line has a finite bandwidth and a point where the absorption reaches a maximum (or the output intensity reaches a minimum). With respect to the present invention, absorption features are important because all the wavelengths that make up the absorbing feature are wavelengths where the gaseous species is absorbing.

Additionally, as used herein, the term "absorption band" is defined as a single uninterrupted wavelength region in the absorption spectrum wherein absorption occurs at each wavelength. Accordingly, if an absorption spectrum contains two absorption lines, $A_1$ and $A_2$, separated by region, B, where no absorption is observed, then two absorbing lines, $A_1$ and $A_2$, correspond to separate absorption bands. If, however, the two absorption lines $A_1$ and $A_2$, are only separated by a local absorption minimum (or local maximum in intensity), then the two absorbing lines, $A_1$ and $A_2$, correspond to a single absorption band. For example, absorption lines that are separate and distinct at a first concentration, may at a second, higher concentration, come together and coalesces to form a single absorption band. It will be appreciated that the temperature, the generation time, and the pumping power will also affect the output spectrum and the measured absorption spectrum. Accordingly, the number of absorbing bands in a measured absorption spectrum will also vary with temperature, generation time, and pumping power.

To analyze the spectral output of the ILS laser 12, the ILS output beam 32 from the ILS laser is sent to the spectrometer assembly 14, which disperses the output beam with respect to wavelength. In FIG. 1a, diffraction gratings 38 and 40 are employed to disperse the output beam 32 exiting the ILS laser 12. Lenses 34 and 36 expand the output beam 32 prior to incidence on the diffraction gratings 38 and 40. Lens 42 focuses the output of the spectrometer assembly 14 onto the optical detector 16.

In one prior art method, (1) the spectrometer assembly 14 contains a dispersive optical element that can be scanned with respect to wavelength, and (2) the optical detector 16 comprises a single channel detector. FIG. 1a depicts this scanning dispersive optical element as a diffraction grating 38.

The spectral signature of the gaseous species in the laser cavity 24 is obtained by scanning the dispersive optical element (grating 38) while the light transmitted through the spectrometer assembly 14 passes through an appropriate aperture 46 placed in front of the (single channel) optical detector 16. (Aperture 46 may simply comprise a slit.) The intensity of the light transmitted through the spectrometer assembly 14 is measured by the optical detector 16 as diffraction grating 38 is scanned.

The optical detector 16 outputs an electrical signal to indicate this intensity. (For example, the electrical signal may be proportional to the ILS laser intensity.) Additionally, the spectrometer sends an electronic signal to the computer 18 that indicates the respective wavelength. In this manner, the computer 18 correlates the intensity determined by the optical detector 16 with the wavelength as determined by the spectrometer assembly 14. Thus, the spectrometer assembly 14 and the optical detector 16 are operated in conjunction with the computer 18 to enable the spectral distribution of the output beam 32 emanating from the ILS laser 12 to be measured.

FIG. 1b schematically illustrates the sort of data obtained from prior art ILS detection methods. Curve 48 represents a typical spectrally dispersed ILS laser output spectrum (or absorption spectrum) obtained by scanning the wavelength and measuring the intensity of the light transmitted through the spectrometer assembly 14. At wavelengths where absorption features are located, the intensity of the ILS laser 12 is attenuated. Arrows 49 indicate six such absorption features. (Curve 50 depicts the spectral distribution of the ILS laser 12 absent any absorbing gaseous species.)

The computer 18 can use the absorption spectrum shown in curve 48 to identify the gaseous species. In particular, the absorption spectrum comprising numerous absorption features within the output spectrum of the ILS laser 12 is measured and compared with the known spectral signature of the gaseous species to be monitored. The positions and relative intensities of the specific absorption features of the gaseous species can be utilized to uniquely identify the gaseous species to be detected. The concentration or amount of the intracavity gaseous species within the laser cavity 24 can be determined from the magnitude of the absorption feature(s) found in the absorption spectrum when the magnitudes are previously calibrated with known concentrations.

In an alternative prior art method, (1) the output beam 32 emanating from the ILS laser 12 is passed through a spectrometer having fixed dispersive optical elements (i.e., gratings 38 and 40 are not scanned), and (2) the optical detector 16 comprises a multichannel detector array. The spectral region over which the ILS laser 12 operates is produced by the spectrometer assembly 14 and is displaced spatially across the (multichannel array) optical detector 16. The aperture 46 (if any) that is placed in front of the optical detector 16 is large enough to allow illumination of a plurality of detectors in the detector array such that multiple wavelengths are simultaneously tracked by the multiple detectors in the detector array.

Accordingly, the specific spectral region that is resolved by the spectrometer assembly 14 is simultaneously measured with the (multichannel array) optical detector 16. The computer 18 operates the (multichannel array) optical detector 16 and reads the intensity measured from the multiple detectors therein. Additionally, the spectrometer assembly 14 sends an electronic signal to the computer 18 that indicates the wavelength resolved by the spectrometer assembly 14. The computer 18 is programmed to convert the electronic signals from the (multichannel array) optical detector 16 and the spectrometer assembly 14 into intensity and wavelength, respectively. In this manner, the computer correlates the intensity determined by the optical detector 16 with the wavelength as determined by the spectrometer assembly 14.

Thus, the spectrometer assembly 14 and the (multichannel array) optical detector 16 are operated in conjunction with the computer 18 to measure and record the spectral distribution of the output beam 32 emanating from the ILS laser 12. An absorption signature similar to that shown in FIG. 1b may be produced.

As described above, the spectral signature is used to identify the gaseous species in the laser cavity 24. The computer records the measured absorption bands comprising numerous absorption features or lines within the output spectrum of the ILS laser 12 and compares them with the known spectral signature of the gaseous species to be monitored. The concentration of the intracavity species can be determined from the magnitude of the absorption feature (s) found in the spectral signature once the magnitudes are calibrated using known concentrations.

It will be appreciated, however, that these prior art methods require the computer 18 to effectively generate a plot of intensity versus wavelength by measuring and recording the intensity at a plurality of wavelengths including the wavelengths corresponding to the absorption features as well as the wavelength regions surrounding the absorption features where absorption is minimal.

The method of the present invention, in contrast, is conceptually much simpler than these prior art approaches. Rather than monitoring the distribution of intensities over a plurality of wavelengths, the method of the present invention involves only determining how much output intensity is produced by the ILS laser 12 during operation, i.e., producing light, within a predetermined wavelength region. The method of the present invention essentially utilizes the overall change in absorption over the entire wavelength region where the ILS laser 12 is operating. Thus, absorption features that were measured in prior art methods by dispersing the laser output are utilized in the present method to affect the total output intensity of the ILS laser 12. Measuring and recording multiple absorption features within the spectrum of the ILS laser 12 is not necessary.

The method of the present invention is conceptually different from the prior art method for ILS gas detection in another respect; namely, the ILS laser 12 used in the present invention preferably has a bandwidth comparable to the bandwidth of the relevant absorption feature(s). Prior art methods of ILS detection employ an ILS laser 12 that has a spectral bandwidth that is substantially larger than the bandwidth of the individual absorption features associated with the intracavity species to be detected. In particular, prior art ILS lasers 12 preferably possess an operational wavelength bandwidth that is at least three times as broad as the absorption features of the gaseous species being monitored. Several reasons tend to favor the use of ILS lasers 12 having a wavelength bandwidth that is substantially broad relative to the bandwidth of the absorption features produced by the gaseous species. As described above, the various absorption features in the spectral signature aid the computer 18 in identifying the particular gaseous species to be detected. Thus, prior art methods of identifying absorbing gaseous species rely on ILS lasers 12 having a spectral bandwidth that is large enough to include more than one absorption feature. Additionally, an ILS laser 12 having multiple longitudinal modes is most advantageous since the enhanced detection sensitivity of ILS techniques derives mainly from the non-linear gain versus loss competition of a multimode laser. Consequently, prior art methods employ ILS lasers 12 that have a spectral bandwidth that is large enough to include multiple longitudinal modes.

The ILS laser 12 of the first embodiment of the present invention, however, preferably has an operational bandwidth that is comparable to or smaller than the bandwidth of one of the absorption bands associated with the intracavity gaseous species being monitored. Additionally, to successfully employ the method of the present invention, the operational bandwidth of the ILS laser 12 must be tuned to directly overlap the absorption band. (As discussed above an absorption band may include a single absorption feature or a plurality of consecutive absorption features.)

The potential or operational bandwidth ($\Delta v_{laser}$) of the ILS laser 12, is defined by the wavelength region over which the gain medium 20 can operate, the spectral characteristics of the mirrors 26 and 28, and the wavelength regions over which each of the optical elements within the optical cavity 24 are transmitting. In particular, $\Delta v_{laser}$ is defined by the convolution of the bandwidth of the gain medium 20 and the mirrors 26 and 28, as well as the bandwidth of any other separate intracavity optical elements, e.g., pellicle or birefringent tuner within the laser cavity 24.

Preferably, the ratio of the operational bandwidth of the ILS laser 12, to the bandwidth of the overlapped portion of the absorption band (comprising, for example, an absorption feature or a plurality of consecutive absorption features) is one to one. More preferably, the operational bandwidth of the ILS laser 12 is (1) sufficiently broad to maintain multimode operation but (2) sufficiently narrow to overlap only the absorption band associated with the gaseous species of interest. The overlapped portion of the absorption band is hereinafter denoted, $W_{abs}$, and its bandwidth, $\Delta v_{abs}$.

As described above, using an ILS laser 12 having a sufficiently broad bandwidth to allow multimode operation preserves the enhanced detection sensitivity that is attainable with ILS. However, since the operational bandwidth of the ILS laser 12 is sufficiently narrow to overlap only the absorption band associated with the gaseous species to be detected, then the intensity of the light output from the laser will be quantitatively altered as the concentration of the gaseous species changes.

When the overlapped portion of the bandwidth of the absorbing gaseous species, $\Delta v_{abs}$, and the bandwidth of the WLS laser 12, $\Delta v_{laser}$, are comparable (i.e., $W_{abs}$ entirely overlaps $W_{laser}$), then absorption from the intracavity gaseous species can limit the amount of light generated by the laser. The ILS laser 12 cannot operate as efficiently in wavelength regions where absorption losses are found. If the absorbing gaseous species is present, then the only region where the ILS laser 12 can operate is occupied by the absorption band, which frustrates the operation of the laser.

With higher concentrations of the gaseous species, the absorption loss will be higher and the task of generating enough light (or gain) in the gain medium 20 to overcome the loss becomes more difficult. Thus, as the concentration of the intracavity gaseous species increases, the intensity of the light output from the ILS laser 12 will decrease. The intensity of the light output as a fuiction of intracavity absorber concentration can be used to calibrate the ILS sensor. This idea can be extended to the special case where at a sufficiently high concentration of absorbing gaseous species, the ILS laser 12 cannot reach threshold at all and will fail to operate. No light output will be produced by the ILS laser.

Consequently, only the intensity of the output of the ILS laser 12 need be monitored in order to quantitatively determine the concentration of the absorbing gaseous species when using the ILS method of the present invention.

Figure 2B:
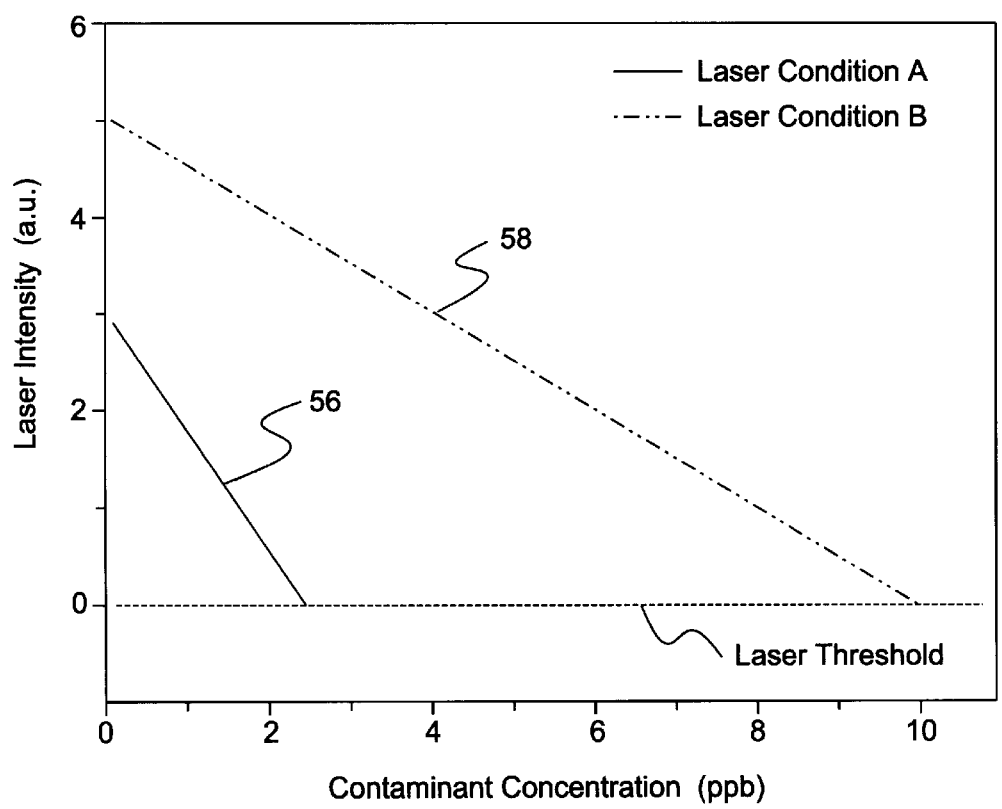
FIG. 2b, on coordinates of intensity and concentration, is a plot of the total output power of the ILS laser of the present invention for two different operational conditions of the ILS laser.

FIGS. 2a and 2b schematically illustrate the method and apparatus of the present invention, which is directed to detecting gaseous species in a gas sample. In particular, FIG. 2a shows a cross-section of an ILS gas detection system 10 constructed in accordance with the present invention and FIG. 2b, on coordinates of intensity and concentration, is a plot of the total output power of the ILS laser of the present invention for three different operational conditions of the ILS laser.

The ILS gas detection system 10 of the present invention simply comprises an ILS laser 12 and an optical detector 16 to quantify either the absolute laser output intensity or the relative change in the laser output intensity.

The ILS laser 12, as depicted in the embodiment of the present invention that is shown in FIG. 2a, includes a gain medium 20, a gas sample cell 22, and a wavelength-selective optical element 52, all of which are situated within an optical resonator 24 formed between mirrors 26 and 28.

Although the laser cavity 24 shown in FIG. 2a is a linear cavity, it will be appreciated that alternative cavity designs can be employed in accordance with the present invention. Such alternative cavity designs are acceptable as long as the potential (or operational) wavelength bandwidth of the ILS laser 12, $\Delta v_{laser}$, is comparable to, i.e., matches one-to-one, or fits within, the overlapped portion of bandwidth, $\Delta v_{abs}$, of the absorption band associated with the gaseous species to be detected.

In the ILS laser shown in FIG. 2a, the wavelength-selective optical element 52 serves to (1) narrow the bandwidth and (2) tune the wavelength of the ILS laser 12. In particular, the wavelength-selective optical element 52 is chosen to ensure that the ILS laser 12 has an operational bandwidth that is not larger than the bandwidth of the overlapped portion of the absorption band. Additionally, the wavelength-selective optical element 52 guarantees that the operational bandwidth of the ILS laser 12 is tuned to coincide with the absorption band comprising, for example, an absorption feature or a plurality of consecutive absorption features.

The wavelength-selective optical element 52 shown in FIG. 2a comprises a metallized pellicle that acts as a thin high-reflectance Fabry-Perot etalon that provides the required narrowband tuning. The metallization increases the finesse of the etalon and narrows the bandwidth thereby creating a narrow-band bandpass filter. Tuning the ILS laser 12 to the appropriate wavelength can be accomplished by rotating the etalon to the angle that passes the desired wavelength. Examples of other wavelength-selective optical elements 52 that may be suitably employed in the present invention include optical bandpass filters, diffraction gratings, prisms, electro-optic bandpass filters, single and multiple plate birefringent filters, and combinations thereof.

It will be appreciated that the potential (or operational) wavelength band, $W_{laser}$, (and bandwidth, $\Delta v_{laser}$) of the ILS laser 12 depends on the gain medium 20 and any optical coatings formed on the optical components that are situated within the laser cavity 24 as well as any optical coatings formed on mirrors 26 and 28. Accordingly, instead of introducing a wavelength-selective optical element 52 into the laser cavity 24, the gain medium and any coatings on the optical components that are used in the ILS laser 12, e.g., mirrors 26 and 28, or windows on the gas sample cell 22, or coatings on crystal 20, can be designed to narrow and tune the potential (or operational) bandwidth, $W_{laser}$, of the ILS laser to overlap only the absorption band associated with the gaseous species to be monitored in the manner described above.

It will be further appreciated that the ILS laser 12 requires a pumping source (not shown) to drive the ILS laser at or slightly above its threshold. For example, an optical pumping source may be employed that delivers optical radiation to the gain medium 20. For the ILS laser 12 depicted in FIG. 2a, however, the potential (or operational) wavelength band of the ILS laser 12, $W_{laser}$, is defined by the convolution of the wavelength band over which the gain medium 20 can operate, the wavelength band over which the mirrors 26 and 28 are reflecting, the wavelength band over which mirror 28 is transmitting, as well as the wavelength band over which any of the other intracavity optical elements (e.g., wavelength-selective optical elements) within the laser cavity 24 are transmitting.

FIG. 2a shows that laser light generated within the gain medium 20 is directed to the gas sample cell 22 and passes through the gas sample therein. As described above, gaseous species within the laser cavity 24 and, in particular, within the gas sample cell 22, may introduce absorption losses. In accordance with the present invention, however, the potential bandwidth, $\Delta v_{laser}$, of the ILS laser 12 is comparable to the bandwidth, $\Delta v_{abs}$, of the overlapped portion, $W_{abs}$, of the absorption band associated with the gaseous species being monitored. Thus, absorption from the intracavity gaseous species will decrease the output power of the ILS laser 12 Therefore, to determine the concentration of the gaseous species, the ILS laser 12 must be calibrated within well-defined operating conditions. The output beam 32 that emanates from the laser is detected directly by an optical detector 16.

In its simplest form, the optical detector 16 comprises a single channel detector such as a photodiode, a photoconductor, or a photomultiplier tube. Other detectors may suitably be employed in the present invention. The only requirement for the optical detector 16 is that the detector must be able to sense the ILS laser beam 32 and produce a resultant electrical signal. Accordingly, an electrical output terminal 54 extending from the optical detector 16 is depicted in FIG. 2a.

The gas detection system 10 of the present invention differs from the prior art system that is shown in FIG. 1a in that no spectrometer assembly 14 nor computer 18 is employed. The gas detection system 10 depicted in FIG. 2a also does not require a scanning dispersive optical element, a multichannel detector array, or a slit that is placed in front of the optical detector 16.

Additionally, the gas detection system 10 shown in prior art does not include a wavelength-selective optical element 52 within the laser cavity 24 that narrows and tunes the operational bandwidth of the ILS laser 12 to coincide only with the absorption band associated with the gaseous species to be detected.

In the prior art methods where the operational bandwidth of the ILS laser 12 is substantially larger than the bandwidth of the overlapped absorbing band, the laser will continue to operate even when large concentrations of the absorbing species are present in the laser cavity 24. Optical losses that are narrow with respect to the overall potential gain bandwidth of the ILS laser 12 will cause the laser to redistribute optical energy into wavelength regions where absorption losses are either absent or reduced. Thus, laser operation will continue but at different wavelengths.

In contrast, the present invention suppresses the redistribution of optical energy into other wavelength regions by ensuring that the absorption losses are a majority fraction of the entire operational bandwidth, $\Delta v_{laser}$, of the ILS laser 12.

It will be appreciated that since ILS offers increased sensitivity beyond prior art methods, weak transitions previously not measured may become measurable for the first time with the gas detection system 10 of the present invention. Knowledge of where to tune the ILS laser 12 must be obtained from spectroscopic studies of the gaseous species of interest that show the spectral location of various absorption features. An understanding of how to optically control the wavelength and operational bandwidth of the ILS laser 12 is also required to match the spectral output of the laser with the absorption feature (or features).

Additionally, to eliminate the possibility of spectral interferences that could lead to false positive readings, spectroscopic studies are required for any additional gaseous species that are likely to be present in a given gas sample. If such additional gaseous species are not to be detected, the spectral output of the ILS laser 12 must be tuned away from any absorbing feature that is produced by these other gaseous species. Potential contributions from absorption features arising from other gaseous species will then be absent in the wavelength region where the ILS laser 12 emits light. Thus, the operational wavelength of the ILS laser 12 must be chosen (1) to coincide with an absorption feature(s) associated with the gaseous species to be detected and (2) to avoid spectral interference from gaseous species that are not of interest. If the foregoing requirements are satisfied, then the spectral interaction with the ILS laser 12 output will be traceable only to absorption from the gaseous species to be monitored. Accordingly, the ILS laser 12 output intensity, when calibrated, will accurately measure the concentration of the monitored gaseous species.

The identity of the gaseous species is known because the selected spectral region over which the ILS laser 12 operates coincides solely with the absorption band associated with the gaseous species being monitored.

The concentration of the gaseous species is known by calibrating the output intensity of the ILS laser 12 under well-defined operating conditions with a known concentration of gaseous species in the laser cavity 24. This concentration depends on a specific set of operational parameters that includes temperature, pressure, laser gain, generation time ($t_g$), i.e., the period over which intracavity mode competition is permitted to occur, and any other parameter that alters the output intensity of the ILS laser 12. It will be appreciated that these operational parameters must be held constant to ensure that the gas detection system 10 remains calibrated. Alternatively, varying these operational parameters will change the calibrated sensitivity of the gas detection system, thus enabling multiple calibrations under different well-defined operational conditions to increase the dynamic range of the gas detection system. Regardless, knowledge of the specific operational parameters that affect the output intensity of the ILS laser 12 is required to design a gas detection system 10 that maintains calibration over extended use. Referring now to FIG. 2b, the output intensity of the ILS laser 12 is shown versus contaminant concentration for two different operational conditions. Curve 56 corresponds to the ILS laser 12 operating closer to threshold where a moderate change in contaminant concentration can produce a more sensitive change in laser output intensity. There is also represented the special case where the contaminant concentration increases to the point that the laser can no longer reach threshold and laser operation ceases. Curve 58 corresponds to the ILS laser 12 operating further above threshold (i.e. higher gain) where the laser output changes less in response to a given change in contaminant concentration than would be the case in the operating condition evidenced by curve 56. However, the dynamic range of the gas detection system is increased under the operating conditions evidenced by curve 58. Curve 58 also represents the special case where the contaminant concentration increases to the point that the laser can no longer reach threshold and laser operation ceases. However, for the operating conditions evidenced by curve 58 the threshold occurs at a higher contaminant concentration.

Figure 3:
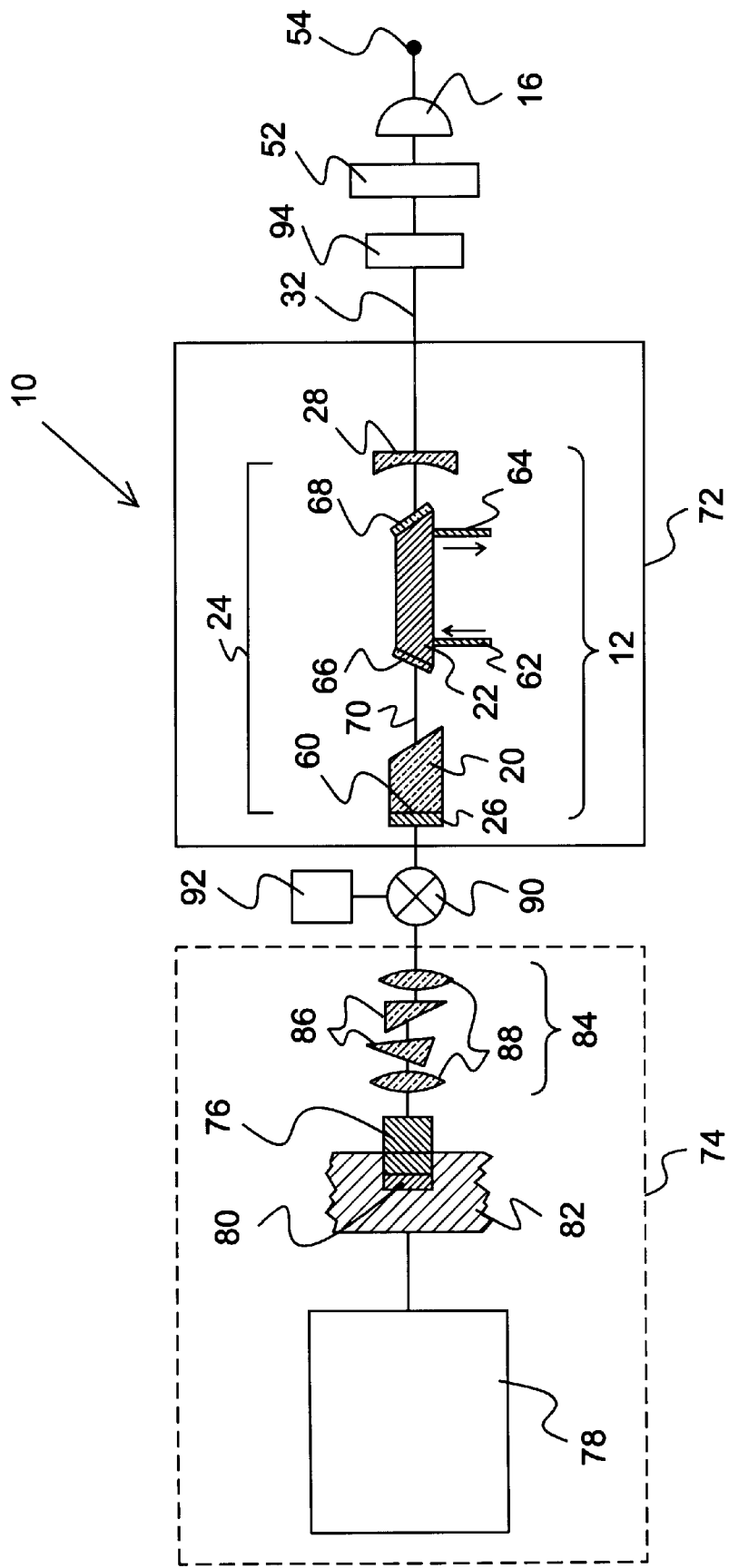
FIG. 3 is a schematic representation of another embodiment of the ILS laser of the present invention.

Referring now to FIG. 3, a separate embodiment of the present invention is shown. In accordance with the present invention, the potential (or operational) wavelength bandwidth ($\Delta v_{laser}$) of the ILS laser 12 depicted in FIG. 3 is narrow enough to coincide exclusively with an absorption band or region ($W_{abs}$) associated with the gaseous species to be monitored. Accordingly, no wavelength-selective optical element 52 is inserted within the laser cavity 24.

As discussed above, the term "absorption band" is defined as a single uninterrupted wavelength region in the absorption spectrum wherein absorption occurs at each wavelength. Accordingly, if an absorption spectrum contains two absorption lines, $A_1$ and $A_2$, separated by region, B, where no absorption is observed, then two absorbing lines, $A_1$ and $A_2$, correspond to separate absorption bands. If, however, the two absorption lines, $A_1$ and $A_2$, are only separated by a local absorption minimum (or local maximum in intensity), then the two absorbing lines, $A_1$ and $A_2$, correspond to a single absorption band.

In accordance with the present invention, the gas detection system 10 depicted in FIG. 3 comprises an ILS laser 12 and an optical detector 16. The ILS laser 12 includes a gain medium 20 that is located within the laser cavity 24 defined by mirrors 26 and 28. The laser cavity 24 is a linear cavity and the gain medium 20 comprises an ion-doped crystal. The first mirror 26 is formed by depositing a reflective coating on one end 60 of the ion-doped crystal. The second mirror 28 comprises a curved reflector.

Although the laser cavity 24 shown in FIG. 3 is a linear cavity, it will be appreciated that alternative cavity designs can be employed in accordance with the present invention. Such alternative cavity designs are acceptable as long as the operational bandwidth, $\Delta v_{laser}$, of the ILS laser 12 is comparable to, i.e., matches one-to-one, or fits within, the bandwidth of the overlapped portion of the absorption band associated with the gaseous species to be detected.

In this second embodiment of the present invention, the ion-doped crystal used as a gain medium 20 is a $Tm^{3+},Tb^{3+}$:YLF crystal. It will be appreciated, however, that other ion-doped crystals may be employed as is suited to the particular use contemplated. Accordingly, it is not intended that the ion-doped crystals specifically disclosed herein, including those listed below, are to be exhaustive.

A sampling of ion-doped crystals that can be suitably employed in the method and apparatus of the present invention include Cr:Tm:Ho:YAG, $Cr^{4+}$:YSO, $Cr^{4+}$:YAG, $Cr^{4+}$:YSAG, $Er^{3+}$:GSGG, $ER^{3+}$:YSGG $Er^{3+}$:YLF, $Er^{3+}$:$Yb^{3+}$:glass, $Ho^{3+}$:YSGG, $Ho^{3+}$:$Tm^{3+}$:LUAG, $Tm^{3+}$:$Ho^{3+}$:YLF, $Tm^{3+}$:$Ho^{3+}$:YAG, $Tm^{3+}$:Ca Y SOAP, $Tm^{3+}$:YLF, $Tm^{3+}$:glass, $Tm^{3+}$:Ca La SOAP, $Tm^{3+}$:YOS, $Tm^{3+}$:YSGG, $Tm^{3+}$:YAG, $Tm^{3+}$:$YVO_4$, $Yb^{3+}$:YAG, Cr:Forsterite, Er:Yb:Glass, $CO_2$:$MgF_2$, $Cr^{2+}$:ZnSe, and $Cr^{2+}$:ZnS/ZnSe/ZnTe. Other materials, whether gas, liquid, or solid, may also be used as the gain medium 20.

FIG. 3 additionally shows a gas sample cell 22 located within the laser cavity 24. The gas sample cell 22 isolates the gas sample from the laser components. It will be appreciated that the gas sample cell 22 is not required for gas samples that are noncorrosive, in which case, the gas sample may be contained within the entire laser cavity 24.

The gas sample cell 22 is provided with an inlet conduit 62 and an outlet conduit 64. Respective cell windows 66 and 68 are mounted on the distal ends of the gas sample cell 22 and permit beam 70 to pass through the gas sample to be analyzed. Windows 66 and 68 also seal the gas sample cell 22.

In the event that gas sample cell 22 is present within chamber 72 containing the ILS laser 12, it is necessary that the gaseous species that are to be detected are removed or eliminated from the chamber. By removing the gaseous species from the chamber 72, the system response obtained through use of the gas detection system 10 accurately indicates the presence and amount of the gaseous species contained within the gas sample cell 22. After purging or evacuating the chamber 72 of gaseous species, the gas sample is fed into the gas sample cell 22 through inlet conduit 62 and outlet conduit 64 (for example, when the gas sample comprises corrosive gas). However, in such cases where the gas sample does not chemically react with the laser components, the gas sample may be communicated into the chamber 72.

As discussed above, the ILS laser 12 requires a pumping source 74 to excite the gain medium 20. Optical excitation of the ion-doped crystal gain medium 20 is provided by the pumping source 74, which comprises a semiconductor diode laser 76.

It should be appreciated that pumping source 74 may comprise any suitable optical pumping source, either coherent or incoherent, continuous or pulsed, that will drive the ILS laser 12. For example, pumping source 74 may alternatively comprise a solid state crystal laser (e.g., Nd:YAG), a gas laser, one or more flashlamps, fiber laser, or any other pumping source that is suitable for pumping the ILS laser 12.

FIG. 3 shows the semiconductor diode laser 76 being powered by an electrical power supply 78 and being cooled by a thermoelectric cooler 80. The semiconductor laser diode 76 and the thermoelectric cooler 80 are mounted in a heatsink 82 provided to dissipate heat generated by the semiconductor diode laser.

Use of a semiconductor diode laser 76 as a pumping source 74, however, typically requires use of a beam shaping optics 84 to facilitate optical matching between the semiconductor diode laser 76 and the ILS laser 12. Examples of beam modification optics include diffractive optics, refractive optics, gradient index optics wherein the refractive index varies axially, gradient index optics wherein the refractive index varies radially, micro-optics, and combinations thereof. FIG. 3 shows the beam shaping optics 84 comprising macroscopic optics, which include a pair of anamorphic prisms 86 and a pair of lenses 88. Alternatively, a beam expanding telescope or micro-optics that are placed within several micrometers of the semiconductor diode laser 76 may be employed.

FIG. 3 further shows a first modulator 90 inserted between the beam shaping optics 84 and the gain medium 20. The first modulator 90 is powered and controlled by a modulator driver 92. The first modulator 90 alternatively attenuates and transmits the pumping beam 96 emanating from the semiconductor diode laser 76 and thereby periodically prevents the pumping beam from pumping the gain medium 20. In this manner, the first modulator 90 causes the pumping beam 96 to reproducibly pump the gain medium 20 such that the ILS laser 12 will be switched on and off.

A second modulator 94 is inserted in the path of the output beam 32 exiting the ILS laser 12. The second modulator 94 alternatively attenuates and transmits the output beam 32 exiting the laser cavity 24 and thereby periodically samples the output beam from the ILS laser 12 by passing the output to the optical detector 16.

The second modulator 94 is synchronized to the first modulator 90 so that the first modulator 90 periodically allows the total intensity of the pumping beam 96 to reach the gain medium 20 while the second modulator 94 periodically allows the total intensity of the output beam 32 to reach the optical detector 16. Use of both modulators, 90 and 94, provides control over the length of time during which the gain in the gain medium 20 is competing with the absorption loss produced by the gaseous species. In particular, the value of $t_g$, generation time, can be adjusted by employing the two modulators, 90 and 94. As used herein, generation time is defined as the period over which mode competition occurs before measurement within the ILS laser 12. (Alternatively, the generation time, $t_g$, can be varied without the use of the first modulator 90 and/or the second modulator 94 by pulsing the output of the pumping source 74 thereby causing the pump beam 96 to alternate between a low intensity and a high intensity value to bring the gain medium 20 alternately below and above (or at) threshold.)

It will be appreciated that interruption in pumping can be achieved utilizing a variety of means, including, but not limited to using a mechanically operated chopper, an electro-optic or acousto-optic modulator, and a shutter. Alternatively, the electrical power supplied to the pumping source 74 (e.g., semiconductor diode laser 76) can be varied, thereby causing the output of the semiconductor diode laser to fluctuate between high and low intensity levels that periodically bring the gain medium 20 just above and below the threshold required for laser operation.

It will be further appreciated that although the second modulator 94 comprises an acousto-optic modulator, other devices such as a mechanically operated chopper or a shutter may be suitably employed in the method and apparatus of the present invention. Alternatively, instead of employing the second modulator 94, optical detector 16 may be alternately switch on and off to periodically sample the output of ILS laser 12.

FIG. 3 depicts the output beam 32 from the ILS laser 12 being directed to the optical detector 16. It will be appreciated that the light output from the ILS laser 12 can alternatively be transmitted via an optical fiber link, i.e., an optical fiber or an optical fiber bundle, to a remote site where the optical detector 16 is located.

As discussed above, the potential (or operational) wavelength band, $W_{laser}$, of the ILS laser 12 of the present invention preferably is narrow enough to coincide exclusively with a single absorption band or region in the absorption spectrum of the gaseous species to be monitored. For the ILS laser 12 shown in FIG. 3, wherein the gain medium 20 comprises $Tm^{+3}$, $Tb^{+3}$:YLF, the wavelength bandwidth directly overlaps a single absorption band in the absorption spectrum of water vapor.

Absorption data for water vapor was obtained using an ILS laser 12 similar to that shown schematically in FIG. 3 except that first modulator 90 was not employed. Rather, the electrical power to the semiconductor diode laser 76 was modulated instead. Additionally, a spectrometer assembly 14 similar to that shown in FIG. 1a was required to disperse the output of the ILS laser 12 to thereby produce the plot depicted in FIG. 4. The ILS laser 12, however, comprised an ion-doped crystal made of $Tm^{+3}$, $Th^{+3}$:YLF that was optically excited with the semiconductor diode laser 76.

Figure 4:
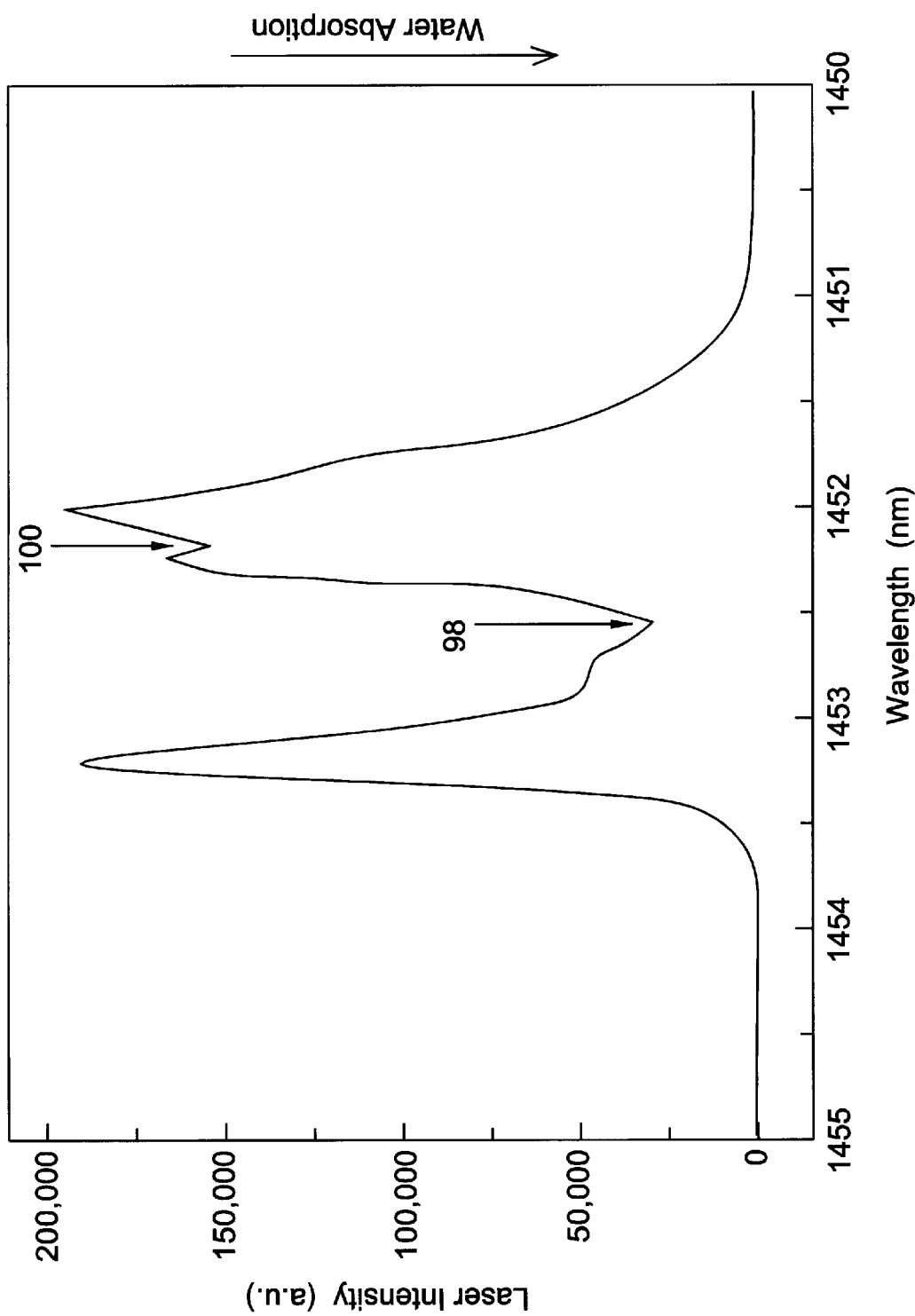
FIG. 4, on coordinates of laser intensity/water absorption (in arbitrary units) and wavelength (in nanometers), is a graph showing the absorption spectrum for high concentrations of water vapor over the wavelengths of 1450 to 1455 nanometers.

FIG. 4 shows a plot of normalized laser intensity/water absorption versus wavelength for a high concentration of water vapor in nitrogen gas. FIG. 4 displays the spectral signature of water vapor for the wavelength region between 1450 to 1455 nanometers in wavelength. Water absorption lines at 1452.5 and 1452.1 nanometers are indicated by arrows 98 and 100, respectively. These two absorption lines are considered absorption features separated by a local minimum in absorption. These two absorption lines have coalesced to thereby form a single absorption band or region that coincides within the bandwidth of the diode pumped $Tm^{+3}$, $Tb^{+3}$:YLF. FIG. 4 depicts the bandwidth of the diode laser-pumped $Tm^{+3}$, $Tb^{+3}$:YLF ILS laser to be roughly comparable to (actually slightly larger than) the water absorption band created by the two water absorption lines. At high enough concentrations, the absorption band or region comprising these two lines will entirely overlap and encompass (i.e., be at least as large as) the operational bandwidth of the ILS laser 12. Accordingly, output intensity from the ILS laser 12 will be reduced or extinguished.

Figure 5:
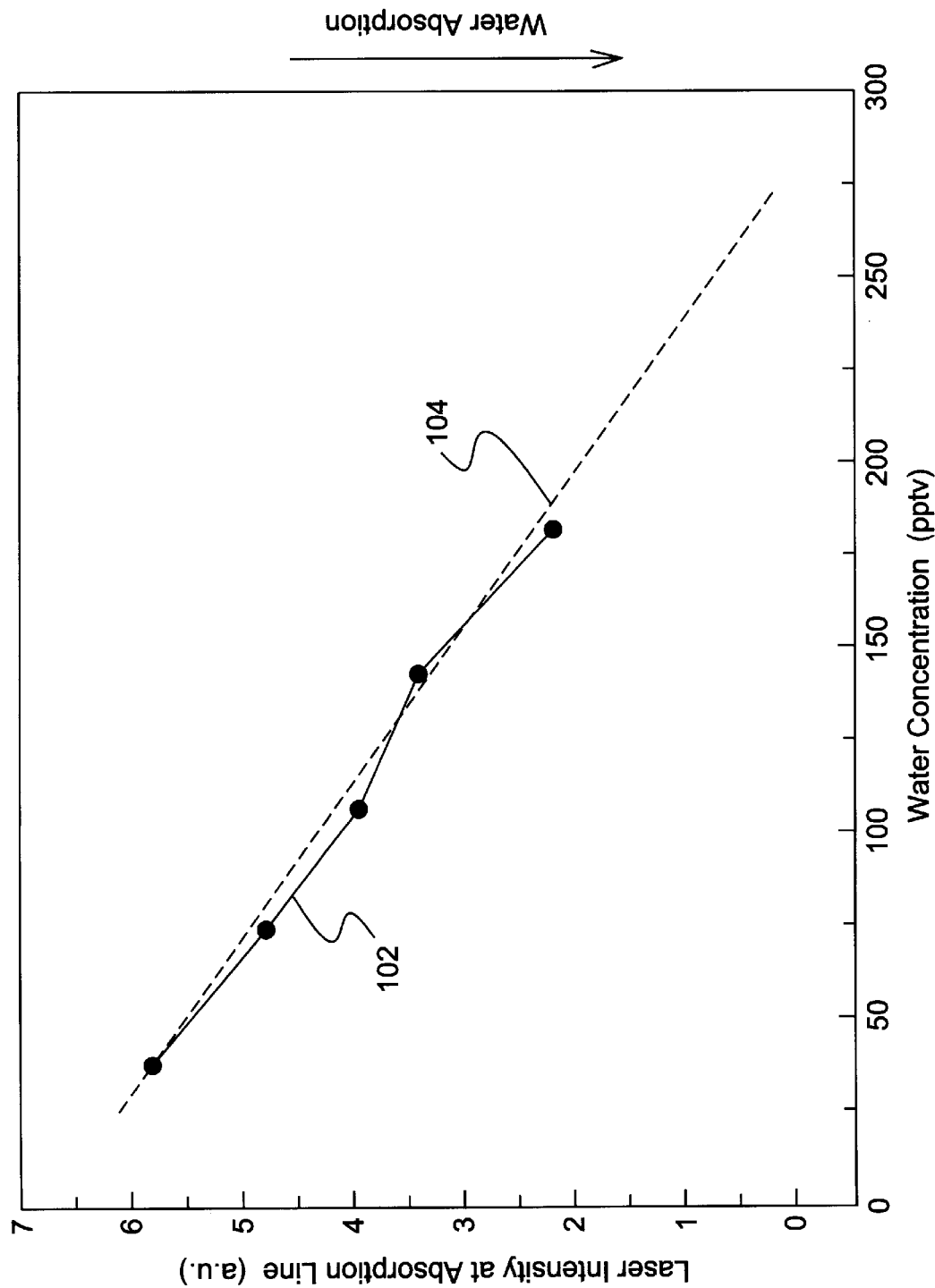
FIG. 5, on coordinates of laser intensity/water absorption (in arbitrary units) and water concentration (in pptv), is a graph showing laser intensity versus water concentration in nitrogen gas as determined by an in-line gas purifier used to remove the water from the nitrogen gas.

A plot of the laser intensity/water absorption versus water concentration in nitrogen gas (in parts per trillion-volume) is shown in FIG. 5. (An in-line gas purifier was used for water purification of the nitrogen gas.) FIG. 5 demonstrates how the intensity of light output from the ILS laser 12 at the absorption line is reduced as concentration increases.

Curve 102, based on experimental data, establishes the trend that increasing concentrations of water vapor will diminish the output intensity of the ILS laser 12.

Curve 104, a fit of curve 102, shows the intensity of the ILS laser 12 as the concentration of water vapor is extrapolated to higher concentrations than shown by curve 102. Curve 104 demonstrates that at sufficiently high concentrations of water vapor the output of the ILS laser 12 will be completely extinguished.

Thus, when the potential or operational bandwidth, $\Delta v_{laser}$, of the ILS laser 12 is comparable to the bandwidth, $\Delta v_{abs}$, of the overlapped portion of the absorption band assigned to the intracavity gaseous species being monitored, the method and apparatus of the present invention can be utilized both to identify and to measure the concentration of the gaseous species.

Utilization of the method of the present invention results in an ILS gas detection system 10 that is substantially smaller, simpler, less expensive, and easier to use than prior art ILS sensors that rely on mapping the wavelength distribution of the output of the ILS laser 12. As a consequence of its smaller size, lower cost, and operational simplicity, the gas detection system 10 of the present invention can be directed to a completely distinct set of applications in gas detection.

Thus, a method and apparatus has been disclosed for detecting the presence of a pre-determined concentration of gaseous species. It will be readily apparent to those skilled in this art that various modifications may be made in the design and arrangement of the elements set forth herein without departing from the scope of the invention as expressed in the appended claims. Moreover, the application of gas detection system 10, as well as the location of the ILS gas detector, e.g., in a semiconductor fabrication assembly, can vary as may be desired. For example, the specific placement of the various elements within the ILS chamber 72 and gas detector system 10 itself may be modified so long as their configuration and placement suitably enables optical excitation of ILS laser 12 in a readily reproducible manner. These and other modifications in the design, arrangement, and application of the present invention as now known or hereafter devised by those skilled in the art are contemplated by the appended claims.

What is claimed is:

1. A gas detection system for detecting the presence of a specific concentration of gaseous species in a gas sample within a calibrated range, said gaseous species absorbing light within at least one single band of consecutive wavelengths, said system comprising:
   (a) an ILS laser comprising:
      (i) a laser cavity; and
      (ii) a gain medium comprising an ion-doped crystal, said ILS laser being configured to operate only at wavelengths entirely included within said at least one band of consecutive wavelengths where said gaseous species is absorbing and said absorbing which induced by said gaseous species is large enough to change the total output intensity of the laser within a calibrated range;
   (b) a container for containing said gas sample in said laser cavity, said container allowing an output beam emanating from said gain medium to pass through said gas sample prior to exiting said laser cavity; and
   (c) a detector for quantifying either the absolute laser output power or the relative change in the laser output power.

2. The gas detection system of claim 1 wherein said ILS laser is configured to operate only within one single region of consecutive wavelengths.

3. The gas detection system of claim 1 wherein said ILS laser comprises components that prevent said ILS laser from operating at wavelengths outside said band where said gaseous species is absorbing.

4. The gas detection system of claim 3 wherein a wavelength-selective optical element is located within said laser cavity, said wavelength selective optical element preventing said ILS laser from operating at wavelengths outside said band where said gaseous species is absorbing.

5. The gas detection system of claim 4 wherein said wavelength selective optical element comprises an intracavity optical element selected from the group consisting of a metallized pellicle that acts as a high-reflectance Fabry-Perot etalon that provides narrow-band tuning, an optical bandpass filter, a diffraction grating, a prism, an electro-optical bandpass filter, a single or multiple plate birefringent filter, and combinations thereof.

6. The gas detection system of claim 3 wherein said gain medium has a bandwidth that is narrow enough to prevent said ILS laser from operating at wavelengths outside said band where said gaseous species is absorbing or has an optical coating thereon that prevents said ILS laser from operating at wavelengths outside said band where said gaseous species is absorbing.

7. The gas detection system of claim 3 wherein said container comprises a gas sample cell located within said laser cavity, said gas sample cell having windows that allow said output beam from said gain medium to pass through said gas sample, at least one of said windows having an optical coating thereon that prevents said ILS laser from operating at wavelengths outside said band where said gaseous species is absorbing.

8. The gas detection system of claim 3 wherein said laser cavity is formed from at least two mirrors and at least one of said mirrors has an optical coating thereon that prevents said ILS laser from operating at wavelengths outside said band where said gaseous species is absorbing.

9. The gas detection system of claim 1 wherein an optical pumping source delivers optical radiation to said gain medium to thereby drive said ILS laser.

10. The gas detection system of claim 1 wherein said gaseous species consists essentially of water vapor.

11. The gas detection system of claim 1 wherein said band where said gaseous species is absorbing comprises a single absorption feature and said ILS laser has an operational bandwidth that is wide enough to maintain multimode operation and narrow enough to overlap only wavelengths in said single absorption feature.

12. The gas detection system of claim 1 wherein said band where said gaseous species is absorbing comprises a plurality of absorption features and said ILS laser has an operational bandwidth that is wide enough to maintain multimode operation and narrow enough to overlap only wavelengths in at least one of said absorption features.

13. A method for detecting the presence of a specific concentration of gaseous species in a gas sample within a calibrated range, said method comprising:
 (a) determining that said gaseous species absorbs light within at least one single band of consecutive wavelengths when said gaseous species is present in said gas sample in quantities within the calibrated range,
 (b) providing an ILS laser comprising:
  (i) a laser cavity; and
  (ii) a gain medium comprising an ion-doped crystal, wherein said ILS laser is configured to operate only at wavelengths entirely included within said at least one band of consecutive wavelengths where said gaseous species is absorbing and said absorption induced by said gaseous species is large enough to change the total laser output intensity of the laser within a calibrated range;
 (c) situating said gain medium such that an output beam from said gain medium is directed through said gas sample that is contained in said laser cavity prior to exiting said laser cavity; and
 (d) situating a detector so as to detect the output intensity exiting said ILS laser to thereby quantify either the absolute output power or the relative change in said ILS laser output power.

14. The method of claim 13 wherein said ILS laser is able to operate only within one single region of consecutive wavelengths.

15. The method of claim 13 wherein said ILS laser includes components therein that prevent said ILS laser from operating at wavelengths outside said band where said gaseous species is absorbing.

16. The method of claim 15 wherein step (b) includes inserting in said ILS laser a wavelength selective optical element that prevents said ILS laser from operating at wavelengths outside said band where said gaseous species is absorbing.

17. The method of claim 16 wherein said wavelength-selective optical element comprises an intracavity optical element selected from the group consisting of a metallized pellicle that acts as a high-reflectance Fabry-Perot etalon that provides narrow-band tuning, an optical bandpass filter, a diffraction grating, a prism, an electro-optical bandpass filter, a single or multiple plate birefringent filter, and combinations thereof.

18. The method of claim 15 wherein said gain medium has a bandwidth that is narrow enough to prevent said ILS laser from operating at wavelengths outside said band where said gaseous species is absorbing or has an optical coating thereon that prevents said ILS laser from operating at wavelengths outside said band where said gaseous species is absorbing.

19. The method of claim 15 additionally comprising inserting a gas sample cell within said laser cavity, said gas sample cell having windows that allow said output beam from said gain medium to pass through said gas sample, at least one of said windows having an optical coating thereon that prevents said ILS laser from operating at wavelengths outside said band where said gaseous species is absorbing.

20. The method of claim 15 additionally comprising forming said laser cavity from at least two mirrors wherein at least one of said mirrors has an optical coating thereon that prevents said ILS laser from operating at wavelengths outside said bands where said gaseous species is absorbing.

21. The method of claim 13 additionally comprising driving said ILS laser with a pumping source comprising an optical pumping source that delivers optical radiation to said gain medium.

22. The method of claim 13 wherein said gaseous species consists essentially of water vapor.

23. The method of claim 13 wherein said band where said gaseous species is absorbing comprises a single absorption feature and said ILS laser has an operational bandwidth that is wide enough to maintain multimode operation and narrow enough to overlap only wavelengths in said single absorption feature.

24. The method of claim 13 wherein said band where said gaseous species is absorbing comprises a plurality of absorption features and said ILS laser has an operational bandwidth that is wide enough to maintain multimode operation and narrow enough to overlap only wavelengths in at least one of said absorption features.

* * * * *